United States Patent [19]

Kelly et al.

[11] Patent Number: 5,011,708
[45] Date of Patent: Apr. 30, 1991

[54] USE OF RADIOACTIVE NICKEL-63 TO INHIBIT MICROBIALLY INDUCED CORROSION

[75] Inventors: James L. Kelly; Ralph J. Reda, both of Charlottesville, Va.

[73] Assignee: University of Virginia Alumni Patents Foundation, Charlottesville, Va.

[21] Appl. No.: 362,000

[22] Filed: Jun. 6, 1989

[51] Int. Cl.$^5$ .................... C23C 14/00; C23C 10/00; C23C 26/00
[52] U.S. Cl. .................... 427/443.1; 427/4; 427/5; 427/438; 204/49; 204/147; 204/148; 204/196; 204/197; 204/192.15
[58] Field of Search .................... 427/443.1, 438, 4, 5; 428/907; 204/192.15, 147, 148, 196, 197, 49

[56] References Cited

U.S. PATENT DOCUMENTS

| 716,678 | 12/1902 | Cuthriell | 428/907 |
| 2,434,291 | 1/1948 | Smith | 428/907 |
| 2,685,535 | 8/1954 | Nack | 427/5 |
| 2,975,073 | 3/1961 | De Long | 427/438 |
| 3,419,419 | 12/1968 | Wright | 427/5 |
| 3,497,434 | 2/1970 | Littauer . | |
| 3,700,482 | 10/1972 | Jacky | 427/5 |
| 3,761,334 | 9/1973 | Zondek | 428/907 |
| 4,017,370 | 4/1977 | Wootten | 427/5 |
| 4,123,338 | 10/1978 | Wootten . | |

FOREIGN PATENT DOCUMENTS

| 3201641 | 7/1983 | Fed. Rep. of Germany | 427/438 |
| 712455 | 1/1980 | U.S.S.R. | 427/438 |
| 1269662 | 4/1972 | United Kingdom | 427/438 |

Primary Examiner—Shrive Beck
Assistant Examiner—Vi D. Dang
Attorney, Agent, or Firm—James C. Wray

[57] ABSTRACT

A method of preventing the growth of microorganisms on the surface of a substrate in contact with the environment, while simultaneously preventing corrosion of these substrates by depositing nickel-63 onto the substrate.

12 Claims, 1 Drawing Sheet

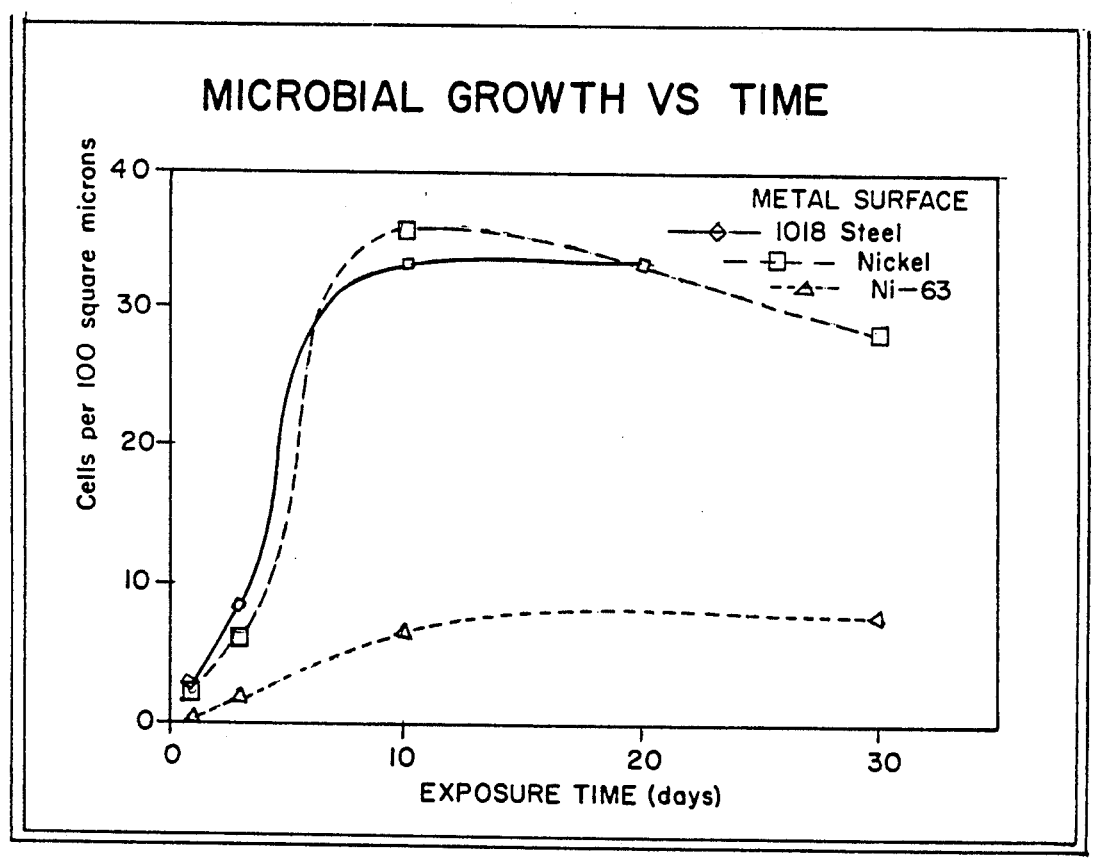

USE OF RADIOACTIVE NICKEL-63 TO INHIBIT MICROBIALLY INDUCED CORROSION

BACKGROUND OF THE INVENTION

1. Field of the Invention

This invention relates to the prevention of microbially induced corrosion, microbial fouling and ordinary electrochemical corrosion by the application of a coating of nickel-63 to the substrate. Specifically, this invention relates to prevention of corrosion of metallic surfaces by microbes.

2. Description of the Prior Art

Microbial corrosion, or microbiologically influenced corrosion (MIC), may be defined as metal loss caused, or accelerated, by microbial action at one or both of the two sites controlling electrochemical corrosion, namely the anode and the cathode. Microbial corrosion has been noted with cast iron, mild steel, stainless steel, aluminum and its alloys, and copper and its alloys. Concrete, wood and various plastics also undergo microbial degradation (by mechanisms that obviously fall outside the above definition for microbial corrosion). The destruction of metallic and non-metallic materials due to microbial action is a serious and costly problem for industrialized societies.

A number of microbes have been identified with degradative processes, including those listed below:

*Cladosporium resinae*—a fungus that corrodes aluminum fuel tanks.

*Pseudomonas*—a type of bacterium capable of reducing ferric iron to ferrous iron.

*Thiobacillus ferrooxidans*—a type of bacterium that oxidizes ferrous iron to ferric iron.

*Thiobaccillus thiooxidans*—a type of bacterium that produces sulfuric acid.

*Gallionnella*—a type of bacterium that can oxidize $Fe^{+2}$ to $Fe^{+3}$.

*Nitrobacter*—a type of bacterium which oxidizes $NO_2^-$ to $NO_3^-$.

*Nitrosomas*—a type of bacterium which oxidizes $NH_3$ to $NO_2$.

*Desulfovibrio, Desulfomonas, Desulfotomaculum*—types of anaerobic, sulfate-reducing bacteria.

The mechanisms by which these microbes contribute to the corrosion of metals and degradation of non-metals are unique to the specific microbes, and many are not well understood. The most widely studied form of microbial attack involves the anaerobic sulfate-reducing bacteria (SRB).

The SRB are found in a variety of natural environments, including many types of soils and sediments, fresh, brackish and salt waters, natural hot springs, oil and gas wells, and sulfur deposits. They tolerate temperatures from <5° to 75° C., a pH range of about 5 to 9.5, and hydrostatic pressures of at least $10^5$ kPa. They survive, but do not grow, under aerobic conditions.

Although there is not universal agreement about the mechanism by which SRB cause or accelerate metallic corrosion, it is believed that the bacteria bring about cathodic depolarization of the metal surface by removing hydrogen from cathodic sites in a sulfate-reducing reaction. The equations for this proposed mechanism are as follows:

(1) anodic reaction $4\ FE \rightarrow 4\ Fe^{+2} + 8\ e^-$ (2) electrolytic dissociation of water $8\ H_2O \rightarrow 8\ H^+ + 8\ OH^-$ (3) cathodic reaction $8\ H^+ + 8\ e^- \rightarrow 8\ H_2O$ (4) cathodic depolarization by SRB $8\ H + SO_4^{-2} \rightarrow S^{-2} + 4\ H_2O$ (5) corrosion product $Fe^{+2} + S^{-2} \rightarrow FeS$ (6) corrosion product $3\ FE^{+2} + 6\ OH^{31} \rightarrow 3\ Fe(OH)_2$ (7) overall reaction $4\ Fe + SO_4^{-2} + 4\ H_2O \rightarrow 3\ Fe(OH)_2 + FeS + 2\ OH^-$ The prevention of microbially induced corrosion usually involves trying to prevent the occurrence, growth and metabolic activity of the microbes in the vicinity of the metal by the use of chemical reagents (biocides), cathodic protection, or protective coatings (e.g. an epoxy film).

U.S. Pat. No. 3,497,434 teaches a method for preventing fouling of a metal structure immersed in a marine environment by coating this metal structure with a metal toxic to marine organism. The metals toxic to marine organisms which are described in this patent are cadmium, tin, zinc and aluminum.

U.S. Pat. No. 4,123,338 describes a method of preventing fouling coupled with corrosion inhibition in water environments by the application of a coating of technetium 99 to the substrate.

SUMMARY OF THE INVENTION

The present invention involves the addition of traces of nickel-63 as an alloying or plating agent to the metal to be protected, with the objective of producing a sufficiently intense radiation field at the surface of the metal so as to inhibit microbial action.

In order for a radioisotope to be suitable as an alloying or plating agent to inhibit microbial corrosion, several conditions must be met, namely, the radioisotope must be compatible with the metal to be protected, it should have a sufficiently long radioactive half-life, it should not render the metal difficult to handle because of the radiation field nor should it present a significant problem with respect to environmental considerations, and it should be available at reasonable prices. Of the few radioisotopes ($^{63}Ni$, $^{90}Sr$, $^{99}Tc$) that meet these criteria, nickel-63 has proven to be the preferred isotope in this method.

Strontium-90 was determined not to be usable principally because of the difficulty in either alloying strontium with steel or depositing a strongly-adhesive coating of SrO to a steel substrate.

The use of Ni-63 instead of TC-99 offers several important advantages, namely:

1. Nickel is a widely used alloying agent with well-documented corrosion-resistant properties, whereas there is relatively little known about the use of technetium as an alloying agent.

2. Nickel may be deposited readily and uniformly onto metallic surfaces by an electroless plating process. On the other hand, there is no evidence that technetium can be deposited by electroless plating. Furthermore, it is quite difficult to achieve uniform depositions of technetium by electrodeposition.

3. Ni-63 has a half-life of 92 y whereas Tc-99 has a halflife of $2.1 \times 10^5$ y. Each Ni-63 isotope is a beta-ray emitter (0.067 MeV max.), emitting beta particles with an average energy of 0.10 MeV. Therefore, to deliver the same radiation dose rate would require a Tc-99 surface loading (in terms of grams of isotope per square centimeter) roughly 800 times greater than the Ni-63 surface loading. Thus, Ni-63 offers a significant advantage in terms of material requirements, resulting in significant advantages with respect to self-shielding.

Further, nickel has several other attractive features:

1. It is readily available from commercial sources.
2. It is a conventional alloying element in many steels and has corrosion-inhibiting properties. It may readily be plated on mild steel plates by an electroless plating process. This process yields a nickel deposit which is less porous than electroplated nickel and which exhibits excellent adhesive properties.
3. Calculations indicate that a Ni-63 deposition of ~30 $\mu$Ci/cm$^2$ will yield a surface radiation intensity of ~100 rad/hr. At a distance of 1 cm. in water or soil, the radiation intensity is almost zero.

These and other and further objects and features of the invention are apparent in the disclosure, which includes the above and ongoing specification, with the claims, and the drawing.

BRIEF DESCRIPTION OF THE DRAWING

FIG. 1 is a graph showing the microbial growth on the radioactive nickel-plated steel, unplated steel and natural nickel-plated steel coupons.

DETAILED DESCRIPTION OF THE INVENTION

Using a method invented by R. L. Boehling, an economical source of nickel-63 is available. This method involves the use of nickel thimble plugs in reactor fuel assemblies instead of conventional steel thimble plugs. Each time a fuel assembly is removed from the core of the reactor, the thimble plug is ordinarily disposed of as radioactive waste material. However, by using and recovering nickel thimble plugs, 300-400 Ci of $^{63}Ni$ (produced by activation of $^{62}Ni$) would be available in each plug removed from the core, with an activity density of 18 2 Ci $^{63}$Ni per cc of nickel. It is estimated that such a production procedure can yield $^{63}$Ni at a cost of roughly $100 per Ci, down significantly from the present cost of roughly $30,000 per Ci for small quantities.

A variation on this idea is to separate the naturally occurring $^{58}$Ni (67.8%) and $^{60}$Ni (26.2%) from $^{62}$Ni (3.7%) and $^{64}$Ni (1.2%) in a gas centrifuge. Then, fabricate the nickel thimble plugs of the $^{62}$Ni/$^{64}$Ni mixture. The result would be to yield a $^{63}$Ni activity of roughly 8000 Ci per thimble plug after its incore exposure was complete.

According to the present invention, nickel-63 is applied to the basic substrate to be protected by any suitable means well known in the prior art. For example, the nickel may be applied to the substrate through the methods of diffusional alloying, melt alloying, electroplating and electroless deposition. As to thickness and composition of the radioactive surface layer, there is no parameter that is particularly critical. Electroplating and electroless plating result in only a surface application and require less nickel radioisotope than alloying. The electroless plating technique is the preferred method over electroplating mainly for the following reasons:

(1) The process produces nickel deposits which are less porous than electroplated nickel and, therefore, have better corrosion resistance in equal thicknesses.

(2) Salt-spray tests and outdoor exposure data indicate that chemically reduced nickel affords better overall corrosion protection to steel than does electrodeposited nickel.

(3) Adhesion of the deposit on mild steel is excellent, exhibiting a tensile strength between 30,000 and 60,000 psi. Specimens show no flaking when pulled to the breaking point of the substrate, or bent 180. over a radius equal to the thickness of the sample.

The nickel which is plated is actually a nickel-phosphorous alloy. The deposition of this ultra-microcrystalline alloy (85 to 97% Ni - 3 to 15% P) is based on the controlled, autocatalytic reduction of nickel cations at an elevated temperature by means of hypophosphite anions in aqueous solution. The probable reactions can be represented by the following equations:

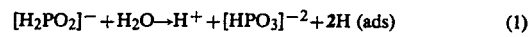  (1)

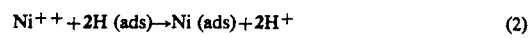  (2)

  (3)

  (4)

The hypophosphate anions, in the presence of water, are dehydrogenated by the solid catalytic surface, e.g., Ni or Fe, to form acid orthophosphate anions. The active hydrogen atoms are absorbed or loosely bonded on the metal surface, which becomes a hydride in the broadest sense. The nickel ions are reduced to metallic nickel by these active hydrogen atoms, the latter being oxidized to hydrogen ions. Simultaneously, a small portion of the hypophosphate anions are similarly reduced by active hydrogen, yielding adsorbed elemental phosphorus, water and hydroxyl ions. The elemental phosphorus is immediately bonded to or dissolved in the nickel, thus making the reaction irreversible. At the same time, more hypophosphate anions are catalytically oxidized to acid orthophosphate anions, with the evolution of gaseous hydrogen.

Following a standard procedure for electroless deposition, ten steel coupons (1"×1") were plated, half with natural nickel, half with $^{63}$Ni-doped nickel. The steel samples were weighed before and after plating so that the mass of the plated Ni-P deposit could be determined. The mass of Ni was assumed to be 90% of the total deposit. Knowing the mass and activity of the nickel initially in the bath, the $^{63}$Ni activity surface density could be calculated for each radioactive specimen. A summary of the deposition data is presented:

| Sample | Mass of Ni-P Deposited, g | Surface Density of Deposited Ni, g/cm$^2$ | Surface Density of Ni-63 Activity $\mu$Ci/cm$^2$ |
| --- | --- | --- | --- |
| 1 | 0.0094 | 0.0017 | 0 |
| 2 | 0.0093 | 0.0017 | 0 |
| 3 | 0.0101 | 0.0018 | 0 |
| 4 | 0.0001 | 0.0015 | 0 |
| 5 | 0.0093 | 0.0017 | 0 |
| 6 | 0.0120 | 0.0023 | 31.2 |
| 7 | 0.0130 | 0.0023 | 31.2 |
| 8 | 0.0144 | 0.0026 | 35.1 |
| 9 | 0.0149 | 0.0027 | 36.3 |
| 10 | 0.0138 | 0.0026 | 35.7 |

Samples 6 and 9 were counted using a Tennelec Model LB 5100 counting system in conjunction with the LB 5110 Processor Controller. The coupons were each placed on a planchet; then the beta counts were taken for 0.10 minutes. The system has a counting efficiency of 31%. The counts and detected activity are:

| Sample No. | CPM | DPM | DPM/cm$^2$ |
|---|---|---|---|
| 6 | 1,319,410 | 4.256 × 10$^6$ | 1.83 × 10$^6$ |
| 9 | 1,289,610 | 4.160 × 10$^6$ | 1.78 × 10$^6$ |

The morphology of the nickel-plated metal surface shows that the coating covers the surface completely, and that the plating is fairly uniform, with the exception of small hemispherical nodules located randomly over the surface.

EXAMPLE

Three coupons each of unplated steel, natural nickel-plated steel, and $^{63}$Ni-doped nickel-plated steel ($\mu$30 $\mu$Ci/cm$^2$) were placed singly into twelve serum vials, and immersed with Postgate's medium C under a nitrogen atmosphere. A deposition of 30 $\mu$Ci/cm$^2$ of Ni-63 produces a surface dose rate of about 10–100 rad/h at the surface of the substrate. The vials were then sealed and autoclaved. Upon cooling, the vials were inoculated with active D. vulgaris and incubated at 25 C. After a certain incubation period, ranging from 1 to 30 days, each vial was opened and the coupon within removed, rinsed with distilled water, and stained with acridine orange. Then, the coupon was rinsed again. Then, a photomicrograph was taken of each coupon's surface with the surface illuminated with ultra-violet light. Ultraviolet light causes acridine orange to fluoresce. Since the bacteria are stained by acridine orange, they may be readily seen and counted in the microscopic field.

The results show that there are no significant differences between the microbial growth on the steel and natural nickel-plated coupons, but that there is a substantial reduction in microbial growth on the radioactive nickel-plated coupons. FIG. 1 shows that the microbial cell density on the radioactive surface is considerably less than on the non-radioactive surfaces.

While the invention has been described with reference to specific embodiments, modifications and variations of the invention may be constructed without departing from the scope of the invention, which is described in the following claims.

We claim:

1. A method for the prevention of microbially induced corrosion or fouling of a substrate, comprising the step of:
    including in or coating on the substrate, prior to its exposure to an environment, an amount of nickel-63 effective to prevent the growth of microorganisms on the substrate;
    and thereafter exposing the substrate to the environment which contains sufficient microorganisms, and for a period of time which would be expected to cause corrosion or fouling of the substrate if not treated.

2. The method of claim 1, wherein the coating is deposited by an electroless deposition.

3. The method of claim 1, wherein the coating is deposited by an electroplating process.

4. The method of claim 1, wherein the coating is deposited by sputtering.

5. The method of claim 1, wherein the coating is deposited by diffusional alloying.

6. The method of claim 1, wherein the coating is deposited by metal alloying.

7. A method for the prevention of microbially induced corrosion or fouling of a substrate, comprising the step of:
    including in or coating on the substrate prior to its exposure to the environment, an amount of nickel-63 sufficient to yield a dose rate of about 10–100 rad/h at a surface of the substrate;
    and thereafter exposing the substrate to the environment which contains sufficient microorganisms, and for a period of time which would be expected to cause corrosion or fouling of the substrate if not treated.

8. The method of claim 7, wherein the coating is deposited by an electroless deposition.

9. The method of claim 7, wherein the coating is deposited by an electroplating process.

10. The method of claim 7, wherein the coating is deposited by sputtering.

11. The method of claim 7, wherein the coating is deposited by diffusional alloying.

12. The method of claim 7, wherein the coating is deposited by metal alloying.

* * * * *